United States Patent [19]

Arretz et al.

[11] Patent Number: 4,985,586

[45] Date of Patent: Jan. 15, 1991

[54] PROCESS FOR THE PREPARATION OF MERCAPTOALCOHOLS

[75] Inventors: Emmanuel Arretz, Pau; Patrick Auge, Billere; Alfred Mirassou, Lescar; Claude Landoussy, Pau, all of France

[73] Assignee: Societe Nationale Elf Aquitaine (Production), France

[21] Appl. No.: 462,987

[22] Filed: Jan. 10, 1990

Related U.S. Application Data

[63] Continuation of Ser. No. 133,617, Dec. 16, 1987, abandoned.

[30] Foreign Application Priority Data

Dec. 30, 1986 [FR] France .................................. 86 18323

[51] Int. Cl.$^5$ ............................................. C07C 331/00
[52] U.S. Cl. ...................................... 560/18; 562/432; 568/62
[58] Field of Search ................. 568/62; 560/9, 18, 57, 560/64, 65, 67; 562/132

[56] References Cited

U.S. PATENT DOCUMENTS

| | | | |
|---|---|---|---|
| 3,290,383 | 12/1966 | Pflugfelder et al. | 260/609 |
| 3,394,192 | 7/1968 | Jones | 568/62 |
| 3,462,496 | 8/1969 | Fletcher et al. | 568/62 |
| 3,662,004 | 5/1972 | Umbach et al. | 568/62 |
| 3,775,463 | 11/1973 | Fischer et al. | 260/471 A |
| 4,281,202 | 7/1981 | Buchholz et al. | 568/62 |
| 4,398,042 | 8/1983 | Kleemann et al. | 568/62 |
| 4,493,938 | 1/1985 | Shimamoto et al. | 568/62 |
| 4,564,710 | 6/1985 | Steger | 568/62 |

FOREIGN PATENT DOCUMENTS

| | | | |
|---|---|---|---|
| 0037891 | 10/1981 | European Pat. Off. | 568/62 |
| 0053171 | 6/1967 | Poland | 568/62 |
| 0182078 | 2/1964 | U.S.S.R. | 568/62 |
| 0988135 | 4/1965 | United Kingdom | 568/62 |
| 2188632 | 10/1987 | United Kingdom . | |

*Primary Examiner*—Bruce Gray
*Attorney, Agent, or Firm*—Morgan & Finnegan

[57] ABSTRACT

This invention relates to improvement to a process for the preparation of mercaptoalcohols containing, more particularly, up to 24 carbon atoms and, preferably, more than 3 carbon atoms, by reaction of the corresponding vicinal epoxides with hydrogen sulphide.

The process comprises incorporating into the reaction mixture a catalyst comprising a guanidine and/or of organic derivatives of a guanidine, and/or of guanidine salts, in particular of guanidine salts. The catalyst can be either in liquid and/or solid form, depending on the nature of the catalyst and its solubility in the reaction mixture, or fixed and/or impregnated into various solid materials. The materials can be organic in nature such as neutral and/or basic polymer resins, polymers or co-polymers, or can be inorganic in nature such as aluminas, silicas, aluminosilicates, zeolites, active charcoals, oxides and/or metal salts.

This process enables mercaptoalcohols to be obtained in a high overall yield while permitting relatively short reaction times.

24 Claims, No Drawings

PROCESS FOR THE PREPARATION OF MERCAPTOALCOHOLS

This application is a continuation of application Ser. No. 133,617, filed Dec. 16, 1987 abandoned.

FIELD OF THE INVENTION

The present invention relates to an improved process for the preparation of mercaptoalcohols from vicinal epoxides and hydrogen sulphide in the presence of new catalysts. The mercaptoalcohols are also known as hydroxy mercaptans, hydroxythiols, thioglycols or else thioalkylene glycols.

BACKGROUND OF THE INVENTION

The preparation of mercaptoalcohols by the reaction of epoxides with hydrogen sulphide is known. Thus, the production of mercaptoethanol by the action of $H_2S$ on ethylene epoxide, or ethylene oxide, has already formed the subject of a certain number of investigations. However, such processes are unsuitable when mercaptoalcohols containing more than 3 carbon atoms are to be prepared.

To this end, Belgian Pat. No. 731,879 proposes the production of mercaptoalcohols from epoxides containing more than 3 carbon atoms. Production is based on the use of strongly basic catalysts such as alkali metal hydroxides, alcoholates and phenolates, and tertiary and/or quaternary onium bases. Belgian Pat. No. 731,881 uses various amines, and U.S. Pat. No. 3,394,192 uses trialkylamines, as other basic catalysts. U.S. Pat. No. 3,462,496 relies on catalysts of the same type: alkali metal or alkaline-earth metal hydroxides, trialkylamines, quaternary ammonium hydroxides or else chromium salts of fatty acids.

More recently, Japanese Patent Application No. 8059160 recommends the addition of carbon disulphide and of alcohols to the reaction of an epoxide with alkali metal hydrogensulphides. Furthermore, U.S. Pat. No. 4,281,202 proposes the use of zeolites in the potassium or sodium form as catalysts. French Pat. No. 2,480,281 describes catalysts consisting of anionic exchange resins, which have previously been the subject of French Pat. No. 1,359,678.

However, particularly for production of mercaptoalcohols containing more than 3 carbon atoms, all these catalysts require relatively long reaction times to finish with a degree of conversion of the epoxide and/or a yield of the desired product which are mediocre or inadequate. Furthermore, the majority of the processes of the prior art take place in the presence of solvents or other additives, even when the reaction mixture remains in the liquid state during the reaction.

SUMMARY OF THE INVENTION

The present invention is intended to overcome the disadvantages of the processes of the prior art. This is achieved using new catalysts permitting mercaptoalcohols to be obtained in higher yields and with higher degrees of conversion of epoxides. The present invention permits relatively short reaction times, and avoids introduction of solvent or other additive into the reaction mixture, except where the reaction mixture is highly viscous or solid.

DETAILED DESCRIPTION

In accordance with the invention, mercaptoalcohols of general formula:

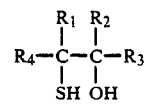

containing more particularly up to 24 carbon atoms and, preferably more than 3 carbon atoms are obtained by the reaction of hydrogen sulphide with the corresponding vicinal epoxides. These epoxides have the formula

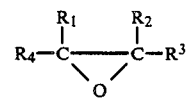

where $R_1$, $R_2$, $R_3$, and $R_4$ may denote hydrogen, a halogen particularly chlorine, a hydroxyl; a $C_1$-$C_{22}$ alkyl, haloalkyl or hydroxyalkyl; $C_2$-$C_{22}$ alkoxyalkyl, alkoxyhaloalkyl or alkylthioalkyl; alkoxyaryls or alkylthioaryls, particularly alkoxyphenyl, which may be optionally substituted by one or more alkyl, halogen, hydroxyl, alkoxy or carboxyl groups or their aliphatic esters; a group containing one or more carboxylic groups; $C_3$-$C_{22}$ alkenyl; $C_5$-$C_{12}$ cycloalkyl or cycloalkenyl; $C_6$-$C_{18}$ aryl or haloaryl; $C_7$-$C_{19}$ aralkyl, aryloxyalkyl, arylthioalkyl, alkylaryl, alkylaryloxyalkyl or alkylarylthioalkyl. When $R_1$ and $R_2$ are taken together, they may denote a $C_3$-$C_{10}$ alkylene. The reaction is carried out in the presence of a catalyst comprising guanidine and/or of guanidine derivatives of general formula:

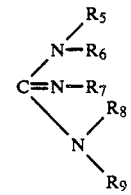

in which $R_5$, $R_6$, $R_7$, $R_8$ and $R_9$ may denote hydrogen, a halogen particularly chlorine, a $C_1$-$C_8$ alkyl, $C_2$-$C_8$ alkenyl, $C_5$-$C_{12}$ cycloaliphatic, $C_6$-$C_{14}$ aromatic, each of these carbon-containing substituents being optionally capable of possessing a halogen such as chlorine and/or a functional group such as hydroxyl and/or ether, and/or of guanidine salts, in particular of guanidine salts such as carbonates, hydrochlorides, sulphates, nitrates, thiocyanates, etc. The catalyst may be either in liquid and/or solid form depending on its nature and its solubility in the reaction mixture. The catalyst may also be fixed and/or impregnated onto various solid materials. These materials may be organic such as neutral and/or basic polymeric resins, polymers or copolymers, or may be of inorganic nature such as aluminas, silicas, aluminosilicates, zeolites, active charcoals, oxides and/or metal salts.

According to the invention, these guanidines generally exhibit a catalytic activity starting with a quantity corresponding to approximately 0.001% by weight relative to the vicinal epoxide, introduced into the reaction mixture. In the majority of cases the upper useful quantity is about 10% by weight. However, it can be exceeded more or less substantially in certain cases of preparation of mercaptoalcohols from higher epoxides containing, for example, more than 18 carbon atoms. The preferred quantity is between 0.1 and 2% by weight. Where a guanidine and/or one of its salts is used fixed and/or impregnated onto a solid material, the quantities of guanidine which are introduced in these forms into the reaction mixture are of the same order, that is from 0.001% to 10% and preferably from 0.1 to 2% relative to the vicinal epoxide contained in the reaction mixture.

The conversion of epoxides into hydroxymercaptans, according to the invention, is promoted by a pressure factor. Thus, it is advantageous to operate between 4 and 25 bars. This permits high degrees of conversion of epoxides into desired products, greater than 90%, to be attained.

It is possible to operate from ambient temperature upwards and, more particularly, between 20° and 100° C. However, the preferred temperature lies in the range from 50° to 80° C.

According to the invention, the reaction of hydrogen sulphide with the vicinal epoxide is carried out by using an $H_2S$/epoxide molar ratio greater than 1 and, preferably, between 1.1 and 1.3. It should be noted that a relatively small excess of $H_2S$, relative to the prior art, permits a very good selectivity for hydroxymercaptan. This excess ensures a very high conversion of the epoxide, which is often higher than 90%.

The reaction time in the process of the invention does not generally exceed 120 minutes. In most cases, it is between 30 and 60 minutes.

In principle, a solvent is not necessary for performing the reaction, in contrast to the majority of the processes of the prior art. However, for highly viscous or solid reaction mixtures, for example of epoxides which remain at least partially in the solid state, it may be useful to include an inert solvent in the operating conditions of the invention. Suitable solvents are: low molecular weight alcohols like methanol, ethanol or propanol; and ethers like dioxane, glycols and/or glycol ethers. For certain epoxides, aliphatic or aromatic hydrocarbons like toluene may be suitable. When $C_2$ or $C_3$ epoxides are involved, the solvent used may be the byproduct of the reaction with $H_2S$, that is to say the corresponding thiodiglycol.

The mercaptoalcohol obtained in this manner is separated from the reaction mixture by conventional means. Preliminary degassing of the unreacted $H_2S$, followed by distillation, preferably under reduced pressure, is an example of such a means.

The practical implementation of the process of the present invention may be performed continuously or non-continuously in stirred or tubular reactors. These reactors can be adapted for operation under pressure and fitted with equipment permitting an efficient control of the high exothermicity of the reaction, such as, among other, jackets and external loops with exchangers.

EXAMPLES

The following examples are intended merely to illustrate the invention and should therefore not be considered to be limiting.

EXAMPLE 1

Invention 206.7 g (1.12 mole) of 1,2-epoxydodecane, to which 1.14 g (0.009 mole) of tetramethylguanidine have been added, are introduced at ambient temperature into a stainless steel reactor fitted with a central stirrer and a jacket. Hydrogen sulphide is then gradually introduced at a controlled rate while the temperature is raised to 74° C., until the $H_2S$/1,2-epoxydodecane molar ratio reaches 1.1. The pressure in the reactor is maintained at 10 bars. Once the injection of $H_2S$ is finished, the mixture is kept reacting for 10 minutes. The total time of the preparation is 35 minutes.

The reaction product, that is 1-mercapto-2-dodecanol, freed beforehand by degassing, from the unreacted dissolved $H_2S$, is recovered at atmospheric pressure, followed by a distillation at a temperature of 118°–120° C., at 0.3 mm Hg. The yield of 1-mercapto-2-dodecanol is 97.2% based on the epoxide used whose degree of conversion is 99%.

Comparative

By way of comparison, the operating procedure of Example 1 is repeated, except that tetramethylguanidine is replaced by triethylamine, representing a catalyst of the prior art, in the same molar proportions relative to 1,2-epoxydodecane. Despite a reaction time increased to 240 minutes, only a 30% conversion of 1,2-epoxydodecane is observed. Hence, production of 1-mercapto-2-dodecanol is well below that of Example 1.

When the preceding test is reproduced, but with a four-fold higher proportion of triethylamine, that is, 0.036 mole for the same quantity of 1,2-epoxydodecane (206.7 g, i.e. 1.12 mole), the degree of conversion of the epoxide can be improved (92%). However, a reaction time of 180 minutes is required, that is considerably longer than that in Example 1.

EXAMPLE 2

Invention

The operating procedure of Example 1 is followed, but with the following modifications:
Epoxide reactant: 1,2-epoxybutane (114 g, i.e. 2 moles)
Catalyst: diphenylguanidine (3.40 g, i.e. 0.016 mole)
$H_2S$/epoxide molar ratio: 1.12
Reaction time: 60 minutes
Temperature: 80° C.
The results are as follows:
Degree of conversion of 1,2-epoxybutane: 96.5%
1-Mercapto-2-butanol yield: 95%.

Comparative

In another series of comparative tests carried out in the operating conditions of Example 1 above, but with the catalysts which are shown below, the results which are summarized in the following table are observed:

| Catalyst (same quantity as that in Example 1) | Degree of conversion of the epoxide, % | Yield of 1-mercapto-2-dodecanol, % |
|---|---|---|
| Diethylamine | 11 | 8 |
| Triethylenetetramine | 23 | 20.5 |
| Benzyltrimethylammonium hydroxide | less than 1— | ... |
| Piperidine | less than 1 | ... |

Also by way of comparison, applying the operating conditions of Example 2 described above, but with the catalyst of the preceding table, the following results are obtained:

| Catalysts (same quantity as that in Example 2) | Degree of conversion of the epoxide, % | Yield of 1-mercapto-2-butanol, % |
| --- | --- | --- |
| Diethylamine | 27 | 24 |
| Triethylenetetramine | 38 | 36 |
| Benzyltrimethylammonium hydroxide | 4 | 3.5 |
| Piperidine | 3.6 | 3 |

It is noted that the above-mentioned four known catalysts give only results which are significantly inferior to those obtained by means of the catalysts of the present invention.

EXAMPLE 3

Invention

An activated alumina possessing a specific surface area of 300 m$^2$/g is impregnated with guanidine carbonate (10 g for 100 g of alumina). 50 g of this solid catalyst are introduced into the reactor described in Example 1, containing 206.7 g (1.12 mole) of 1,2-epoxydodecane. Hydrogen sulphide is introduced gradually at a controlled rate while the temperature is raised to 74° C., until the H$_2$S/1,2-epoxydodecane molar ratio reaches 1.1. The pressure in the reactor is maintained at 10 bars. Once the injection is finished, the mixture is kept reacting for 80 minutes. The yield of 1-mercapto-2-dodecanol is 95% based on the epoxide used, whose degree of conversion is 98%.

EXAMPLE 4

Comparative

A series of experiments is carried out, in which an anionic ion exchange resin, Amberlyst A-21, is used as a basic catalyst. The same operating procedure is repeated with the reactor described in Example 1. The initial charge of 1,2-epoxydodecane is 206.7 g (1.12 mole), and hydrogen sulphide is introduced at a controlled rate until the H$_2$S/1,2-epoxydodecane molar ratio reaches 1.1. The temperature is raised to 74° C. The pressure in the reactor is maintained at 10 bars. Once the injection of H$_2$S is finished, the mixture is kept reacting for the time required to convert the 1,2-epoxydodecane. The first test consisted in using Amberlyst A-21 resin in the 100 ml reactor. After a 4 hours reaction at 74° C., the degree of conversion of 1,2-epoxydodecane is 83%; and the yield of 1-mercaptododecanol is 81.4%.

For the second test, the same quantity of Amberlyst A-21 resin (100 ml) is kept, but this time 1,2-epoxydodecane (206.7 g) is introduced with 0.009 mole of triethylamine. A very marked increase in the reaction speed is found, given that after 4 hours the conversion of 1,2-epoxydodecane reached 94%; and the yield of 1-mercapto-2-dodecanol is 92.4%.

Invention

A similar test is carried out with the triethylamine replaced with the same molar quantity of tetramethylguanidine. The synergistic effect between guanidine and the Amberlyst A-21 anionic resin is still much greater, given that 1,2-epoxydodecane is completely converted after 25 minutes.

Lastly, a final test is carried out with a charge of Amberlyst A-21 anionic resin which had been preimpregnated with guanidine carbonate (10%). Under the same conditions as in the preceding tests, the conversion of 1,2-epoxydodecane is 98.5% after a 90 minutes reaction. The 1-mercapto-2-dodecanol yield obtained is 95%.

EXAMPLE 5

Invention

Applying the same operating procedure as in Example 1, 149.5 g (1.15 mole) of butyl glycidyl ether $$CH_2\underset{O}{\overset{}{\diagdown\diagup}}CH-CH_2OC_4H_9$$

are reacted at 80° C., in the presence of 0.3 g of tetramethylguanidine, with hydrogen sulphide in a H$_2$S/epoxide molar ratio equal to 1.13. Reaction time is 45 minutes.

The degree of conversion of butyl glycidyl ether is 98% and the 3-butoxy-1-mercapto-2-propanol (HS—CH$_2$—CHOH—CH$_2$OC$_4$H$_9$) is obtained with 95% yield.

Comparative

When tetramethylguanidine is replaced by 1 g of triethylamine, the conversion degree of butyl glycidyl ether is only 89% and the yield of mercaptoalcohol is only 79%.

EXAMPLE 6

Invention

Applying the same operating procedure as in Example 1, 214 g (1.15 mole) of 2-ethylhexyl glycidyl ether $$CH_2\underset{O}{\overset{}{\diagdown\diagup}}CH-CH_2-O-CH_2-CH(C_2H_5)-C_4H_9$$

are reacted at 84° C., in the presence of 0.6 g of tetramethylguanidine, with hydrogen sulphide in a H$_2$S/epoxide molar ratio equal to 1.15. The reaction time is 40 minutes.

The conversion degree of the epoxide is 99% and the mercaptoalcohol HS—CH$_2$—CH(OH)—CH$_2$—O—CH$_2$CH(C$_2$H$_5$)—C$_4$H$_9$ is obtained with a 97% yield.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. A process for preparing a mercaptoalcohol of formula:

$$R_4-\underset{\underset{SH}{|}}{\overset{\overset{R_1}{|}}{C}}-\underset{\underset{OH}{|}}{\overset{\overset{R_2}{|}}{C}}-R_3$$

containing up to 24 carbon atoms, comprising reacting hydrogen sulphide with the corresponding vicinal epoxide, of formula:

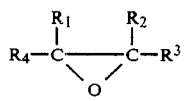

wherein $R_1$, $R_2$, $R_3$ and $R_4$ denote hydrogen, halogen, a hydroxyl; a $C_1$–$C_{22}$ alkyl, haloalkyl or hydroxyalkyl; $C_2$–$C_{22}$ alkoxyalkyl, alkoxyhaloalkyl; alkoxyaryl which may be optionally substituted by one or more alkyl, halogen, hydroxyl, alkoxy or carboxyl groups or their aliphatic esters; $C_3$–$C_{22}$ alkenyl; $C_5$–$C_{12}$ cycloalkyl or cycloalkenyl; $C_6$–$C_{18}$ aryl or haloaryl; $C_7$–$C_{19}$ aralkyl, alkylaryl; and when $R_1$ and $R_2$ are taken together they may denote a $C_3$–$C_{10}$ alkylene, the reaction is carried out in the presence of a catalyst selected from the group consisting of guanidine, guanidine carbonate, guanidine hydrochloride, guanidine sulphate, guanidine nitrate, guanidine thiocyanate, and guanidine derivatives of formula:

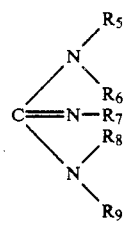

in which $R_5$, $R_6$, $R_7$, $R_8$ and $R_9$ may denote hydrogen atoms or a $C_1$–$C_8$ alkyl, $C_2$–$C_8$ alkenyl, $C_5$–$C_{12}$ cycloaliphatic or $C_6$–$C_{14}$ aromatic radicals, each of the carbon-containing radicals optionally including a halogen, hydroxyl or ether group, and recovering said mercaptoalcohol.

2. The process according to claim 1, wherein the concentration of catalyst is from 0.001 to 10% by weight relative to the quantity of epoxide introduced into the reaction mixture.

3. The process according to claim 1, wherein the reaction time does not exceed about 120 minutes.

4. The process according to claim 3, wherein the reaction time is between 30 and 60 minutes.

5. The process according to claim 1, wherin the reaction is performed at a pressure of from about 4 to 25 bars.

6. The process according to claim 1, wherein the reaction is performed without solvent or other additive.

7. The process according to claim 1, wherein the reaction temperature is between 20° and 100° C.

8. The process according to claim 7, wherein the reaction temperature is between 50° and 80° C.

9. The process according to claim 1, wherein the molar ratio of the reactants $H_2S$/epoxide is between 1.1 and 1.3.

10. The process according to claim 1, wherein an inert solvent is used, the solvent being low molecular weight alcohols, ethers like dioxane, glycols, glycol ethers, or an aliphatic or aromatic hydrocarbon like toluene.

11. The process according to claim 1, wherein the mercaptoalcohol contains at least three carbon atoms.

12. The process according to claim 1, wherein the catalyst is fixed or impregnated into organic or inorganic solid materials.

13. The process of claim 1, wherein the catalyst is guanidine carbonate, diphenylguanidine or tetramethylguanidine.

14. The process according to claim 13, wherein the concentration of catalyst is from 0.001 to 10% by weight relative to the quantity of epoxide introduced into the reaction mixture.

15. The process according to claim 13, wherein the reaction time does not exceed about 120 minutes.

16. The process according to claim 15, wherein the reaction time is between 30 and 60 minutes.

17. The process according to claim 13, wherein the reaction is performed at a pressure of from about 4 to 25 bars.

18. The process according to claim 13, wherein the reaction is performed without solvent or other additive.

19. The process according to claim 13, wherein the reaction temperature is between 20° and 100° C.

20. The process according to claim 19, wherein the reaction temperature is between 50° and 80° C.

21. The process according to claim 13, wherein the molar ratio of the reactants $H_2S$/epoxide is between 1.1 and 1.3.

22. The process according to claim 13, wherein an inert solvent is used, the solvent being low molecular weight alcohols, ethers like dioxane, glycols, glycol ethers, or an aliphatic or aromatic hydrocarbon like toluene.

23. The process according to claim 13, wherein the mercaptoalcohol contains at least three carbon atoms.

24. The process according to claim 13, wherein the catalyst is fixed or impregnated into organic or inorganic solid materials.

* * * * *